US009651492B2

(12) United States Patent
Segawa et al.

(10) Patent No.: US 9,651,492 B2
(45) Date of Patent: *May 16, 2017

(54) OPTICAL DETECTOR

(71) Applicant: Sony Corporation, Tokyo (JP)

(72) Inventors: Yuji Segawa, Tokyo (JP); Tasuku Yotoriyama, Tokyo (JP); Shinichi Kai, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/948,972

(22) Filed: Nov. 23, 2015

(65) Prior Publication Data

US 2016/0077006 A1 Mar. 17, 2016

Related U.S. Application Data

(63) Continuation of application No. 14/581,161, filed on Dec. 23, 2014, now Pat. No. 9,228,950, which is a (Continued)

(30) Foreign Application Priority Data

May 14, 2009 (JP) ................................ P2009-117731
Aug. 12, 2009 (JP) ................................ P2009-187342

(51) Int. Cl.
*G01N 21/64* (2006.01)
*B01L 3/00* (2006.01)
*B01L 7/00* (2006.01)

(52) U.S. Cl.
CPC ...... *G01N 21/6454* (2013.01); *B01L 3/50851* (2013.01); *B01L 7/52* (2013.01);
(Continued)

(58) Field of Classification Search
CPC ..... B01L 2300/0627; B01L 2300/1827; B01L 3/50851; B01L 7/52; G01N 21/6454
See application file for complete search history.

(56) References Cited

U.S. PATENT DOCUMENTS 5,307,144 A 4/1994 Hiroshi et al.
6,287,871 B1 9/2001 Herron et al.
(Continued)

FOREIGN PATENT DOCUMENTS

JP 2001-139654 5/2001
JP 2003-525617 9/2003
(Continued)

OTHER PUBLICATIONS

Japanese Office Action issued Feb. 19, 2013 in corresponding Japanese Patent Application No. 2009-187342.
(Continued)

*Primary Examiner* — Nathan Bowers
*Assistant Examiner* — Lydia Edwards
(74) *Attorney, Agent, or Firm* — K&L Gates LLP

(57) ABSTRACT

Disclosed herein is an optical detector at least including: a first substrate in which a plurality of wells are formed; a second substrate in which a heating section is provided to heat the wells; a third substrate in which a plurality of photoirradiation sections are provided in alignment with the wells; and a fourth substrate in which a plurality of photodetection sections are provided in alignment with the wells.

9 Claims, 5 Drawing Sheets

Related U.S. Application Data continuation of application No. 12/775,044, filed on May 6, 2010, now Pat. No. 8,945,911.

(52) U.S. Cl.
CPC .. *G01N 21/6428* (2013.01); *B01L 2300/0627* (2013.01); *B01L 2300/0654* (2013.01); *B01L 2300/1822* (2013.01); *B01L 2300/1827* (2013.01); *G01N 2201/068* (2013.01)

(56) References Cited

U.S. PATENT DOCUMENTS

| | | |
|---|---|---|
| 2004/0038390 A1 | 2/2004 | Boege et al. |
| 2005/0133724 A1 | 6/2005 | Hsieh et al. |
| 2006/0030037 A1 | 2/2006 | Joseph et al. |
| 2006/0073491 A1 | 4/2006 | Joseph et al. |
| 2007/0002309 A1* | 1/2007 | Yamamoto ........... G01N 21/253 356/39 |
| 2007/0238089 A1 | 10/2007 | Rosenthal et al. |
| 2008/0176290 A1* | 7/2008 | Joseph ................ G01N 21/253 435/91.2 |
| 2008/0280350 A1* | 11/2008 | Moriwaki ................ B01L 7/52 435/286.1 |
| 2009/0060795 A1 | 3/2009 | Owen et al. |
| 2010/0105035 A1 | 4/2010 | Hashsham et al. |

FOREIGN PATENT DOCUMENTS

| | | |
|---|---|---|
| JP | 2003-298068 | 10/2003 |
| JP | 2004-25426 | 1/2004 |
| JP | 2005-172429 | 6/2005 |
| JP | 2005-345439 | 12/2005 |
| JP | 2006-047153 | 2/2006 |
| JP | 2008-237207 | 10/2008 |
| JP | 2008-278832 | 11/2008 |
| JP | 2009-022202 | 2/2009 |
| JP | 2009-097982 | 5/2009 |

OTHER PUBLICATIONS

European Patent Office, Extended European Search Report, issued in connection with European Patent Application No. 10004655.6, dated Apr. 17, 2012. (6 pages).

European Communication Pursuant to Article 94(3) issued Jun. 3, 2016 in corresponding European Application No. 10004655.6.

* cited by examiner

OPTICAL DETECTOR

CROSS REFERENCES TO RELATED APPLICATIONS

The present application is a continuation of U.S. patent application Ser. No. 14/581,161, filed Dec. 23, 2014, which application is a continuation of U.S. patent application Ser. No. 12/775,044, filed May 6, 2010, issued as U.S. Pat. No. 8,945,911 on Feb. 3, 2015, which application claims priority to Japanese Priority Patent Application JP 2009-187342 filed in the Japan Patent Office on Aug. 12, 2009, and in Japanese Priority Patent Application JP 2009-117731 filed in the Japan Patent Office on May 14, 2009 the entire contents of which is hereby incorporated by reference.

BACKGROUND

The present application relates to an optical detector and, more particularly, to an optical detector for use in gene expression analysis, infectious disease testing, gene analysis such as SNP (Single Nucleotide Polymorphism) analysis, protein analysis, cell analysis and other analyses.

Recent years have seen an increasing commercialization of hybridization detection techniques including DNA (deoxyribonucleic acid) chip or DNA microarray. DNA chip is a large number of varied DNA probes packed and immobilized on a substrate surface. Detection of hybridization on the substrate surface of this DNA chip allows for all-inclusive analysis of gene expression and other processes in cells and tissues.

The data obtained from this micro array is verified by means of the realtime PCR (Polymerase Chain Reaction) method. This is a standard approach for quantitative analysis of nucleic acid in trace amounts. The realtime PCR method permits amplification of DNA and other target several-hundreds-of-thousand-fold by repeating the amplification cycle including "thermal denaturation, annealing with a primer and polymerase elongation reaction." The realtime PCR method is used to monitor in realtime the PCR amplification product obtained as described above for quantitative analysis of nucleic acid in trace amounts. In this method, a dedicated device incorporating a thermal cycler and fluorescence spectrophotometer in a single unit is used to monitor in realtime the PCR amplification product.

In addition to the PCR method, there are other nucleic acid amplification techniques such as the SMAP (SMart Amplification Process), LAMP (Loop-Mediated Isothermal Amplification), NASBA (Nucleic Acid Sequence Based Amplification) and ICAN (Isothermal and Chimeric primer-initiated Amplification of Nucleic acid) methods designed to isothermally amplify DNA. Here, however, a description will be given below of the realtime PCR detection method, a typical amplification method.

First, if only the gene target of interest can be amplified using a highly specific primer, the intercalator method using SYBR (registered trademark) GreenI is employed.

In the intercalator method, an intercalator is used which emits fluorescence when bonded to a double-chain DNA. Fluorescence is emitted by bonding this intercalator to a double-chain DNA produced in the course of PCR reaction and irradiating excitation light onto the intercalator. The amount of PCR amplification product generated is monitored by detecting the intensity of this fluorescence. This intercalator method requires no designing or synthesis of a fluorescent labeling probe specific to the target, making it readily applicable for measurement of a wide variety of targets.

On the other hand, if it is necessary to distinguish between sequences having similar structures or if multiplex detection is required as for typing of SNPs, a probe method is used. The TaqMan (registered trademark) probe method is an example of such a probe method and uses, as a probe, an oligonucleotide having its 5' end modified with a quencher substance and its 3' end modified with a fluorescent substance.

The TaqMan probe specifically hybridizes to a template DNA in the annealing step. The same probe does not emit fluorescence when irradiated with excitation light due to the presence of a quencher substance on the probe. In the elongation reaction step, however, the TaqMan probe hybridized to the template DNA is decomposed by a 5' to 3' exonuclease activity of the TaqDNA polymerase. As a result, the fluorescent substance is liberated from the probe, eliminating the inhibition by the quencher and causing fluorescence to be emitted. The amount of PCR amplification product generated can be monitored by detecting the intensity of this fluorescence.

A detailed description will be given below of the steps for quantifying gene expression level by the above methods using realtime PCR. First, PCR is performed on a serially diluted standard sample of known concentration as a template to find the threshold cycle (Ct value) required to reach a given amount of amplification product. A standard curve is prepared by plotting this Ct value along the horizontal axis and the initial DNA amount along the vertical axis. Based on this, PCR reaction is performed on a sample of unknown concentration under the same conditions to find the Ct value. Finally, the DNA amount of interest in the sample is measured from this Ct value and standard curve.

As for the techniques related thereto, JP-T-2003-525617 and Japanese Patent Laid-Open No. 2001-136954 (hereinafter referred to as Patent Documents 1 and 2, respectively) disclose, for example, temperature control and other techniques during amplification reaction.

SUMMARY

An optical detector must measure the reactions taking place in the wells in realtime. For example, an optical detector for use in nucleic acid amplification detection must measure the nucleic acid amplification process in realtime. As a result, such a detector must include not only wells in which reactions are conducted but also a variety of means. Such means include heating means adapted to accelerate the respective reactions, photoirradiation means adapted to irradiate excitation light and photodetection means adapted to detect fluorescence and other light from the wells.

A recent significant advance in biotechnology holds promise for development of more compact optical detectors with higher accuracy.

In light of the foregoing, according to the present invention, a high performance and compact optical detector that can be readily manufactured is provided.

First, an embodiment of the present application provides an optical detector. The optical detector includes at least first, second, third and fourth substrates. A plurality of wells are formed in the first substrate. Heating means is provided in the second substrate to heat the wells. A plurality of photoirradiation means are provided in the third substrate. The plurality of photoirradiation means are aligned with the wells. A plurality of photodetection means are provided in the fourth substrate. The plurality of photodetection means are aligned with the wells.

In the optical detector according to an embodiment, the necessary means are provided one in each substrate. This makes it possible to manufacture the optical detector simply by stacking the substrates one on the other.

The heating means may be provided across the second substrate. Alternatively, the plurality of heating means may be aligned with the wells on the second substrate.

The heating means that can be used for the optical detector according to an embodiment is not specifically limited in structure so long as the wells can be heated. As an example, the heating means can be configured by patterning transparent electrodes in the second substrate.

In this case, ITO and ZnO electrodes are among transparent electrodes that can be used.

On the other hand, the wells can be heated from either side of the wells by the heating means. For example, the second substrate may be stacked on the side of the first substrate facing the third or fourth substrate. Alternatively, the second substrates may be stacked one on each side of the first substrate in such a manner as to sandwich the first substrate so as to heat the wells from both sides.

The optical detector according to an embodiment need only include at least the first to fourth substrates. However, a plurality of condenser lenses may be arranged between the photoirradiation means and wells or between the wells and photodetection means.

The optical detector according to an embodiment can serve as a nucleic acid amplification detector capable of detecting nucleic acid amplification in the wells.

In this case, the optical detector according to an embodiment permits nucleic acid amplification not only by means of the PCR (Polymerase Chain Reaction) method, a widely used technique for gene amplification, but also by means of isothermal amplification methods such as the SMAP (SMart Amplification Process) method, LAMP (Loop-Mediated Isothermal Amplification) method, ICAN (Isothermal and Chimeric primer-initiated Amplification of Nucleic acids) method and NASBA (Nucleic Acid Sequence-Based Amplification) method.

In the optical detector according to an embodiment, the necessary means are provided one in each substrate and aligned with each other. This makes it possible to readily manufacture a high performance and compact optical detector simply by stacking the substrates one on the other.

Additional features and advantages are described herein, and will be apparent from the following Detailed Description and the figures.

DETAILED DESCRIPTION

Figure 1:
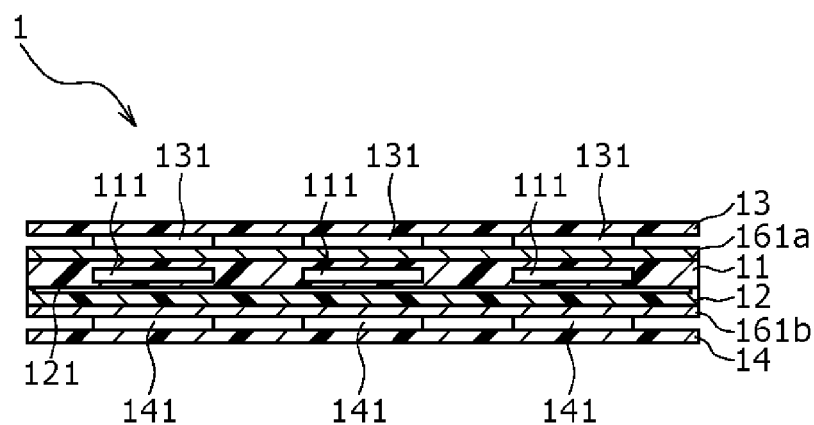
FIG. 1 is a sectional schematic view schematically illustrating a first embodiment of an optical detector.

The present application will be described in detail below with reference to the figures according to an embodiment. It should be noted that the description will be given in the following order:

(1) Wells 111 (first substrate 11)
(2) Heating portion 121 (second substrate 12)
(3) Photoirradiation portion 131 (third substrate 13)
(4) Photodetection portion 141 (fourth substrate 14)
(5) Condenser lenses 151*a*, 151*b* and 151*c*
(6) Optical filters 161*a*, 161*b* and 161*c*
(7) Apertures 181*a*, 181*b*, 181*c*, 181*d* and 181*e* and partition walls
(8) Specific example of the optical detector FIG. 1 is a sectional schematic view schematically illustrating a first embodiment of an optical detector 1 according to the present invention. The optical detector 1 includes at least a (1) first substrate 11, (2) second substrate 12, (3) third substrate 13 and (4) fourth substrate 14. The optical detector 1 may further include (5) condenser lenses 151*a* and 151*b* and (6) optical filters 161*a* and 161*b* as necessary.

The materials used to form the respective substrates are not specifically limited, and any of those materials that can be commonly used for optical detectors such as nucleic acid amplification detectors can be selected as desired. In the present invention, it is particularly preferred that the substrates be made of a light-transmitting material such as polycarbonate, polyolefin-based resin, acryl-based resin or other plastic resin, PDMS (polydimethylsiloxane) or other silicon-based resin or glass so as to allow light to transmit through the substrates.

A detailed description will be given below of the substrates of the optical detector 1 according to an embodiment and the means provided in the substrates.

(1) Wells 111 (First Substrate 11)

A plurality of wells 111 are formed in the first substrate 11. The wells 111 are reaction fields where interactions proceed between the substances such as nucleic acid amplification, hybridization, nucleic acids, proteins and cells.

If the optical detector 1 according to an embodiment is used as a nucleic acid amplification detector, any of the methods used as the gene amplification methods can be selected as desired for nucleic acid amplification. For example, among the methods that can be used are the PCR method, SMAP method, LAMP method, ICAN method, NASBA method, SDA (Strand Displacement Amplification) method, TMA (Transcription-Mediated Amplification) and TRC (Transcription-Reverse transcription Concerted) method. Of these methods, an isothermal amplification method such as the SMAP, LAMP, ICAN or NASBA method should preferably be used. The isothermal amplification methods do not require any temperature variation as does the PCR method, thus eliminating the need for a heat radiation mechanism and making the device as a whole compact.

In the optical detector 1 according to an embodiment, excitation light is irradiated from one side of the first substrate 11 in which the wells 111 are formed so as to detect light such as fluorescence emitted from the substances in the wells 111 from the other side of the first substrate 11. Therefore, it is preferred that the wells 111 be made of a light-transmitting material such as polycarbonate, polyolefin-based resin, acryl-based resin or other plastic resin, PDMS (polydimethylsiloxane) or other silicon-based resin or glass.

Figure 2:
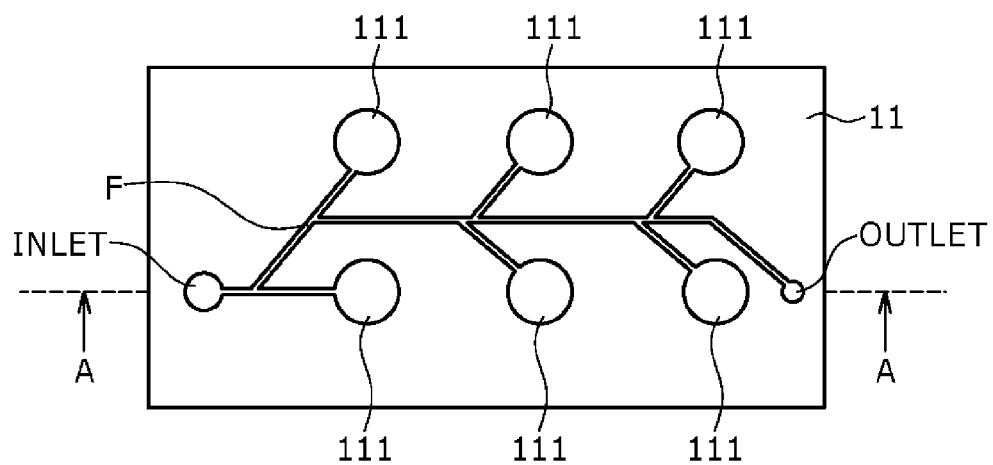
FIG. 2 is a plan schematic view schematically illustrating an example of a first substrate of the optical detector according to an embodiment.
Figure 3:
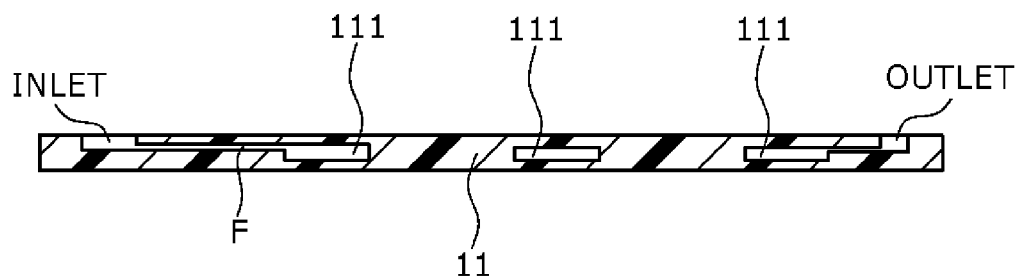
FIG. 3 is an A-A fragmentary sectional view as seen from an arrow A-A of the example of the first substrate shown in FIG. 2.

It should be noted that the method used to introduce the substances into the wells 111 is not specifically limited, and any of the publicly known methods can be used as desired. As illustrated in FIGS. 2 and 3, for example, a flow path F leading to the wells 111 can be formed in the substrate to introduce the substances into the wells 111 via the flow path F.

(2) Heating Portion 121 (Second Substrate 12)

A heating portion 121 is provided in the second substrate 12 to heat the wells 111. The heating method used for the heating portion 121 is not specifically limited, and any of the publicly known methods can be used as desired. For example, electrodes may be patterned in the substrate.

Figure 4:
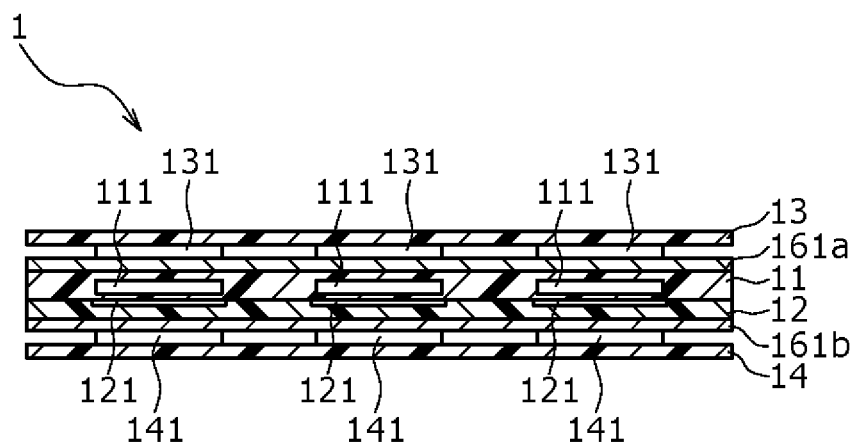
FIG. 4 is a sectional schematic view schematically illustrating a second embodiment of the optical detector.

The heating portion 121 is not specifically limited in form so long as it can heat the wells 111. As illustrated in FIG. 1, the heating portions 121 may be provided across the second substrate 12 to heat the wells 111 as a whole. Alternatively, the heating portions 121 may be aligned, one with each of the wells 111, as illustrated in a second embodiment of FIG. 4. If the heating portions 121 are provided, one for each of the wells 111, it is possible to control the heating temperature and time for each of the wells with precision.

If the heating portions 121 are provided, one for each of the wells 111, it is preferred that the heating portion 121 be designed to be larger than the wells 111. Although the heating efficiency of the heating portion 121 may be lowered at the edges, the heating portion 121 larger than the wells 111 can suppress the reduction in heating efficiency at the edges.

As for the control method, temperature sensors may be provided in the heating portion 121, although not shown, so as to feed back the measured temperatures, thus permitting accurate control of the temperatures.

Further, if the heating portions 121 are provided, one for each of the wells 111, it is possible to locally heat the wells 111, thus contributing to reduced power consumption. Assuming, for example, that the nine wells of about 100 nL each are heated at 60° C. for 30 minutes by means of the SMAP method, if nine ITO electrodes are used, the power consumption is on average about 0.6 W. On the other hand, if Peltier devices are used, the power consumption is on average about 10 W, which is an order of a magnitude greater than if ITO electrodes are used.

Further, if the heating portions 121 are provided, one for each of the wells 111, it is possible to control the temperatures of the individual wells 111, thus preventing variations in temperature from one well to another.

Still further, using electrodes as the heating portion 121 allows for reduction in size of the detector. For example, if Peltier devices are used, ceramic plates for thermal diffusion must be provided on top of the Peltier devices to provide uniform temperature distribution. Further, Peltier devices require heatsinks and fans for heat radiation and absorption, thus requiring a thickness of about 30 mm. On the other hand, transparent electrodes such as ITO or ZnO electrodes require only the thickness of the second substrate (e.g., 0.7 mm) for patterning the same electrodes, thus contributing to reduced size of the detector as a whole.

Figure 5:
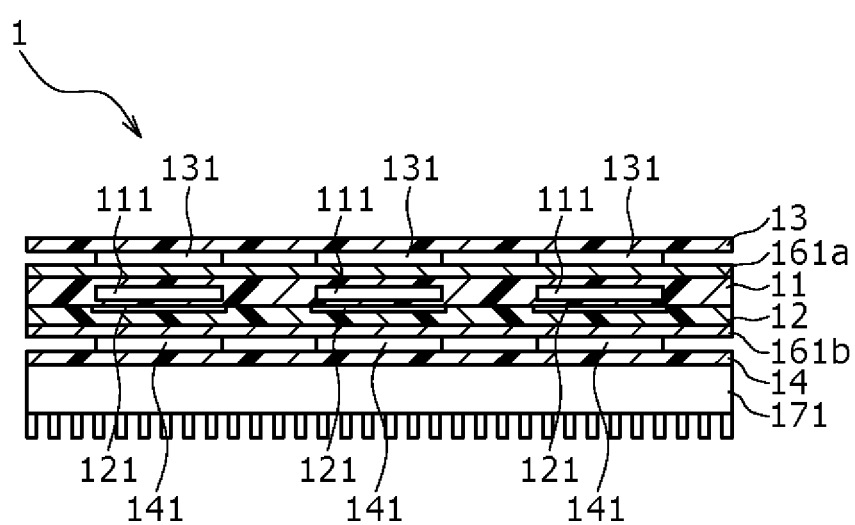
FIG. 5 is a sectional schematic view schematically illustrating a third embodiment of the optical detector.

It should be noted that the heating portion 121 using electrodes may be combined with a Peltier device as illustrated in a third embodiment of FIG. 5. If, for example, a constant-temperature Peltier device 171 of 20 to 40° C. is used in combination, hunting of the heating portion 121 using electrodes during temperature control will be suppressed, thus providing stable temperature regulation.

The second substrate 12 having the heating portion 121 is stacked on the first substrate 11 having the wells 111 formed therein. As a result, the heating portion 121 must also transmit excitation light from photoirradiation portion 131 or fluorescence or other light from the substances. Therefore, if electrodes are used as the heating portion 121, transparent electrodes must be used. In this case, ITO and ZnO electrodes are among transparent electrodes.

Figure 6:
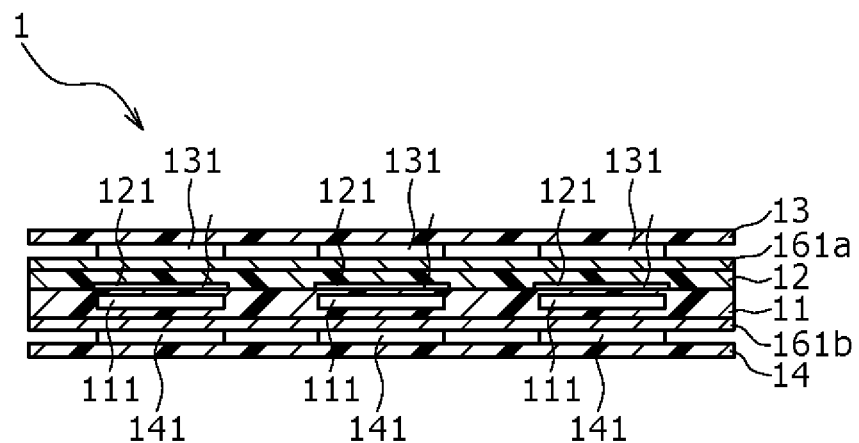
FIG. 6 is a sectional schematic view schematically illustrating a fourth embodiment of the optical detector.

The wells 111 can be heated by the heating portion 121 from either side of the wells 111. The direction of heating is not limited to an upward direction from bottom in the figure as in the first embodiment of FIG. 1, second embodiment of FIG. 4 and third embodiment of FIG. 5. Instead, the wells 111 may be heated from top in the figure as in a fourth embodiment of FIG. 6.

If, for example, transparent electrodes such as ITO or ZnO electrodes are used as the heating portion 121, the transmittance thereof may decline as a result of heating. However, if the heating portions 121 are provided above the wells 111 in the figure (on the side facing the third substrate 13 which will be described later), light emitted from the wells 111 can be detected properly by photodetection portions 141 which will be described later, thus providing improved S/N ratio.

Figure 7:
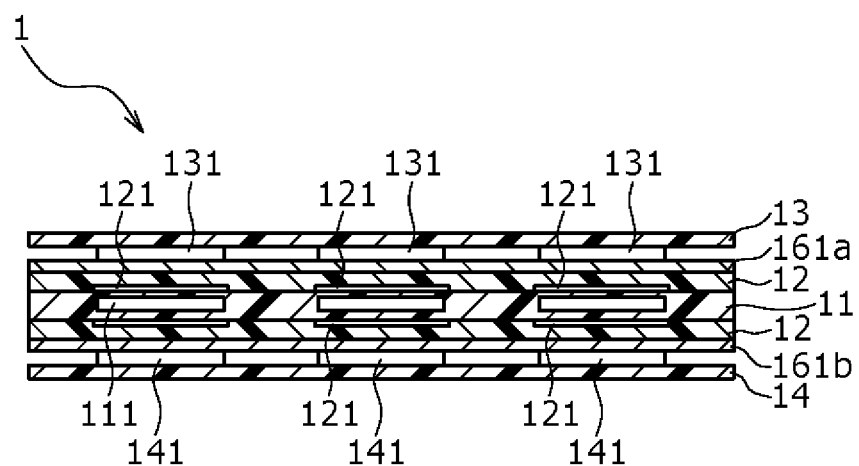
FIG. 7 is a sectional schematic view schematically illustrating a fifth embodiment of the optical detector.

Further, the wells 111 may be, for example, heated from both sides as in a fifth embodiment of FIG. 7. Heating the wells 111 from both sides provides an advantageous effect in that the well temperatures can be readily maintained uniform.

The heating portions 121 of the optical detector 1 according to the embodiment of the present invention are provided in the second substrate 12. This makes it possible to readily change the heating direction simply by changing the position where the second substrate 12 is stacked on the first substrate 11 having the wells 111 formed therein. For example, if the second substrate 12 is stacked on top of the first substrate 11 in the figure (on the side facing the third substrate 13 which will be described later), the wells 111 can be heated from top. On the other hand, if the two second substrates 12 are made available and stacked one on either side of the first substrate 11 in such a manner as to sandwich the first substrate 11, the wells 111 can be heated from both sides.

Still further, if the second substrate 12 is stacked under the first substrate 11 in the figure (on the side facing the fourth substrate 14 which will be described later), it is preferred that the lower side of the second substrate 12 be anti-reflection coated, although not shown. Anti-reflection coating is expected to provide 3 to 5% improvement in transmittance in the visible range.

(3) Photoirradiation Portion 131 (Third Substrate 13)

The plurality of photoirradiation portions 131 are provided in the third substrate 13 in such a manner as to be aligned with the wells 111. The photoirradiation portions 131 are designed to irradiate excitation light, for example, onto the fluorescent substances in the wells 111 and onto the intercalator.

Thanks to the plurality of photoirradiation portions 131 of the optical detector 1 according to an embodiment provided in the third substrate 13 in alignment with the wells 111, it is possible to irradiate light onto the wells 111 with accuracy simply by stacking the third substrate and first substrate 11 one on the other. This eliminates the need to align the photoirradiation portion with the wells 111 for scanning, thus requiring no drive mechanism adapted to move the photoirradiation portion and contributing to reduced size of the detector.

On the other hand, if excitation light is irradiated from a single photoirradiation portion onto the plurality of wells in a single operation, a long optical path is required to eliminate chromaticity, making the increase in size inevitable for detectors in related art. In the optical detector 1 according to the embodiment of the present invention, however, light can be irradiated onto the wells 111 in a single operation simply by stacking the third substrate 13 having the photoirradiation portion 131 and the first substrate 11 having the wells 111 formed therein one on the other. This also contributes to reduced size of the detector.

The photoirradiation method that can be used for the photoirradiation portion 131 of the optical detector 1 according to the embodiment of the present invention is not specifically limited, and any of the publicly known methods can be used as desired. For example, one or two or more photoirradiation methods can be selected as desired. Among selectable irradiation methods are LED (Light Emitting Diode), semiconductor laser and EL lighting.

The signal acquisition time can be reduced by lighting up the photoirradiation portions 131 in a single operation and detecting the light with the photodetection portions 141, which will be described later, in a single operation. Alternatively, noise from the adjacent photoirradiation portions 131 can be reduced by lighting up the same portion 131 quickly one after the other.

(4) Photodetection Portion 141 (Fourth Substrate 14)

The plurality of photodetection portions 141 are provided in the fourth substrate 14 in alignment with the wells 111. The photodetection portions 141 are designed to detect light from the fluorescent substances in the wells 111 and the intercalator so as to monitor the amount of amplification product generated in the wells 111.

Thanks to the plurality of photodetection portions 141 of the optical detector 1 according to an embodiment provided in the fourth substrate 14 in alignment with the wells 111, it is possible to detect light such as fluorescence from the wells 111 with accuracy simply by stacking the fourth substrate and first substrate 11 one on the other. This eliminates the need to align the photodetection portions with the wells 111 for scanning, thus contributing to reduced size of the detector.

The photodetection method that can be used for the photodetection portion 141 of the optical detector 1 according to the embodiment of the present invention is not specifically limited, and any of the publicly known methods can be used as desired. Among selectable detection methods are those using area imaging device such as PD (Photo Diode), charge coupled device (CCD) and complementary metal oxide semiconductor (CMOS).

(5) Condenser Lenses 151a, 151b and 151c

Figure 8:
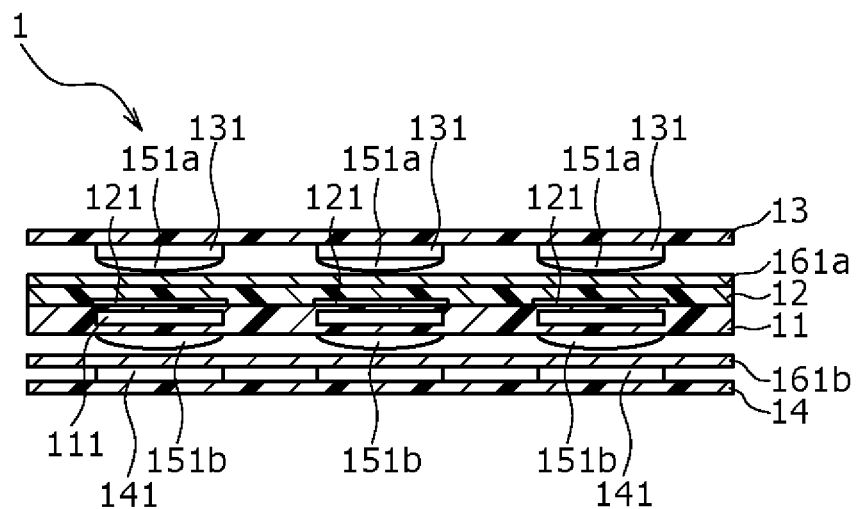
FIG. 8 is a sectional schematic view schematically illustrating a sixth embodiment of the optical detector.

FIG. 8 is a sectional schematic view schematically illustrating a sixth embodiment of the optical detector 1 according to an embodiment. In the present embodiment, a plurality of excitation condenser lenses 151a are provided between the photoirradiation portions 131 and wells 111 to collect light from the photoirradiation portions 131. The optical detector 1 according to the embodiment of the present invention permits accurate irradiation of light onto the wells 111 simply if the third substrate and first substrate 11 are stacked one on the other. However, the optical detector 1 permits even more accurate irradiation if the excitation condenser lenses 151a are provided as in an embodiment.

Further, in the present embodiment, a plurality of photoreception condenser lenses 151b are provided between the wells 111 and photodetection portions 141 to focus light such as fluorescence from the wells 111 onto the photodetection portions 141. The optical detector 1 according to an embodiment permits accurate detection of light from the fluorescent substances in the wells and the intercalator simply if the fourth substrate and first substrate 11 are stacked one on the other. However, the levels of fluorescence and other signals can be enhanced further if the photoreception condenser lenses 151b are provided as in the present embodiment, thus providing improved S/N ratio.

Figure 9:
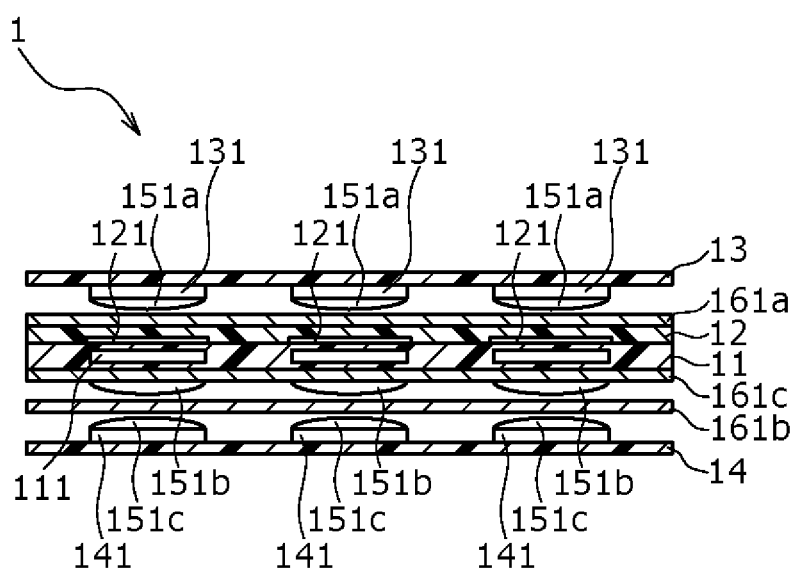
FIG. 9 is a sectional schematic view schematically illustrating a seventh embodiment of the optical detector.

Still further, in the optical detector 1 according to an embodiment, a plurality of second photoreception condenser lenses 151c may be provided in addition to the photoreception condenser lenses 151b as in a seventh embodiment shown in FIG. 9. If the two condenser lenses 151b and 151c with a short focal distance and high numerical aperture are provided for each of the wells as the photoreception condenser lenses as described above, it is possible to provide even higher fluorescence collection efficiency, thus ensuring even higher S/N ratio. Further, close proximity imaging is possible, making it possible to shorten the optical system and contributing to reduced size of the detector. Still further, distortion of the substrates at the edges can be reduced without using a combination of expensive lenses as in a microscope, thus allowing for photodetection at a brightness equivalent to that at the center of the substrate. Moreover, crosstalk from the adjacent wells can be reduced if the focal distance of the second photoreception condenser lenses 151c is equal to or shorter than that of the first photoreception condenser lenses 151b.

(6) Optical Filters 161a, 161b and 161c

In the optical detector 1 according to an embodiment, the excitation optical filter 161a may be provided between the photoirradiation portions 131 and wells 111 (refer to FIGS. 1 and 4 to 10). If the excitation optical filter 161a is provided, it is possible to selectively irradiate excitation light of desired wavelength onto the wells 111. The optical detector 1 according to the embodiment of the present invention permits accurate photoirradiation onto the wells 111 simply if the third substrate and first substrate 11 are stacked one on the other. However, if the excitation optical filter 161a is provided, it is possible to selectively irradiate excitation light with more accuracy according to the properties of the fluorescent substances in the wells 111 and the intercalator.

In the optical detector 1 according to an embodiment, the photoreception optical filter 161b may be provided between the wells 111 and photodetection portions 141 (refer to FIGS. 1 and 4 to 10). If the photoreception optical filter 161b is provided, it is possible to selectively receive light of desired wavelength from among light such as fluorescence from the fluorescent substances in the wells 111 and the intercalator. The optical detector 1 according to the embodiment of the present invention permits accurate detection of light from the substances in the wells 111 simply if the fourth substrate and first substrate 11 are stacked one on the other. However, if the photoreception optical filter 161b is provided, it is possible to selectively obtain light with more accuracy, thus providing improved S/N ratio.

Further, in the optical detector 1 according to an embodiment, a second photoreception optical filter 161c may be provided between the first substrate 11 and first photoreception condenser lenses 151b in addition to the first photoreception optical filter 161b as illustrated in a seventh embodiment of FIG. 9. As described above, the insertion of one more photoreception optical filter enhances removal of excitation light irradiated from the photoirradiation portion 131, thus providing further improved S/N ratio.

(7) Apertures 181a, 181b, 181c, 181d and 181e and partition walls

Figure 10:
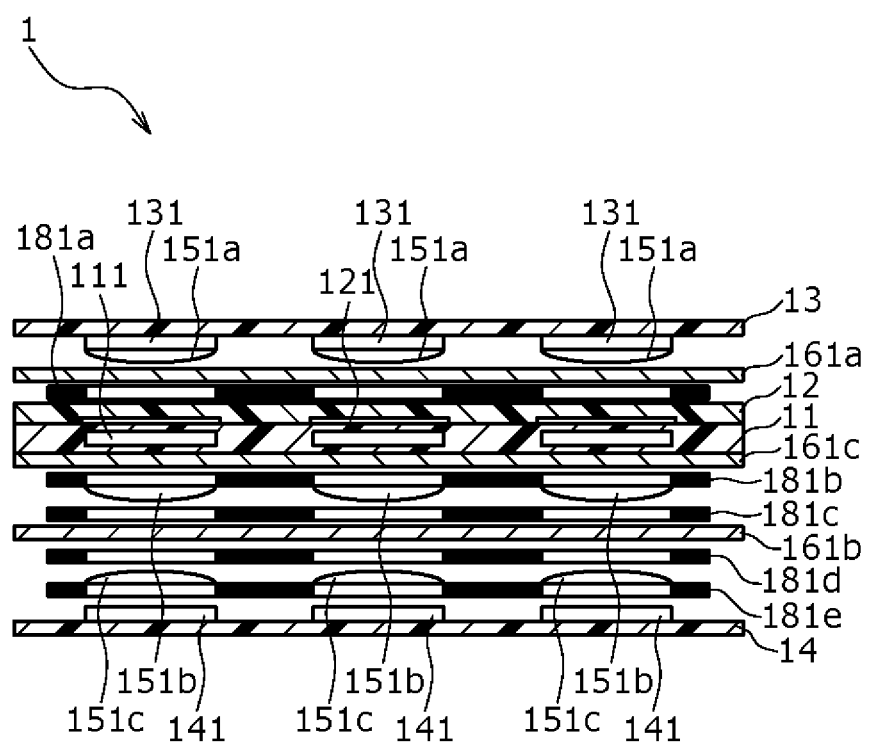
FIG. 10 is a sectional schematic view schematically illustrating an eighth embodiment of the optical detector.

FIG. 10 is a sectional schematic view schematically illustrating an eighth embodiment of the optical detector 1. In the present embodiment, apertures 181a, 181b, 181c, 181d and 181e are provided, one between the excitation optical filter 161a and second substrate 12, and one on each side of the photoreception condenser lenses 151b and 151c. It should be noted that the optical detector 1 according to an embodiment provides the same advantageous effect if partition walls, although not shown, rather than the apertures 181a, 181b, 181c, 181d and 181e, are provided between the lenses.

As described above, the aperture 181a or partition wall on the photoirradiation side prevents irradiation of light from the photoirradiation portion 131 onto the wells 111 other than the associated one (e.g., adjacent wells), thus providing improved S/N ratio.

On the other hand, the apertures 181b, 181c, 181d and 181e or partition walls on the photodetection side provides reduced crosstalk from the wells 111 other than the associated one (e.g., adjacent wells), thus providing improved S/N ratio.

The optical detector 1 according to an embodiment described above permits a variety of detections and analyses not only on medical frontlines but also in other wide ranging fields, including on-site diagnosis in developing countries and disaster-hit areas, detection of pathogenic bacteria in food processing plants, food warehouses, grocery stores and restaurants, detection in food-producing areas, environmental testing in seas, lakes and rivers and environmental testing for norovirus in public facilities.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An optical detecting apparatus configured to detect a signal from a sample in at least one of a plurality of wells, the optical detecting apparatus comprising:
   heaters configured to control temperatures in the plurality of wells, the heaters including a plurality of pairs of first and second heaters positioned apart to accommodate at least one of the wells in alignment between each respective pair of heaters, the wells being positioned apart from the first and second heaters;
   light sources configured to illuminate the sample, the light sources being arranged on a first side of the first heaters that is opposed to a well accommodation side of the first heaters;
   optical detection elements configured to detect a signal from the sample, the optical detection elements being arranged on a second side of the second heaters that is opposed to a well accommodation side of the second heaters; and
   a plurality of apertures provided in at least one position of: between the wells and the light sources; and between the wells and the optical detection elements.

2. The optical detecting apparatus of claim 1, wherein the heaters include patterned transparent electrodes.

3. The optical detecting apparatus of claim 2, wherein the transparent electrodes are ITO or ZnO electrodes.

4. The optical detecting apparatus of claim 1, wherein a plurality of condenser lenses are provided, each of the condenser lenses being provided in alignment between respective opposed light sources and first heaters.

5. The optical detecting apparatus of claim 1, wherein a plurality of condenser lenses are provided, each of the condenser lenses being provided in alignment between respective opposed optical detection elements and second heaters.

6. The optical detecting apparatus of claim 1, wherein a plurality of condenser lenses are provided, a pair of the condenser lenses being provided in alignment between respective opposed optical detection elements and second heaters.

7. The optical detecting apparatus of claim 6, wherein an optical filter is provided in alignment between the two condenser lenses for each pair of condenser lenses.

8. The optical detecting apparatus of claim 1, configured as a nucleic acid amplification detector capable of detecting nucleic acid amplification in the wells.

9. The optical detecting apparatus of claim 1, further comprising a constant-temperature Peltier device provided on a side of the optical detection elements such that the optical detection elements are sandwiched between the second heaters and the constant-temperature Peltier device.

* * * * *